United States Patent
Eckles et al.

(10) Patent No.: US 8,374,209 B2
(45) Date of Patent: Feb. 12, 2013

(54) MULTI-PASS OPTICAL CELL WITH ACTUATOR FOR ACTUATING A REFLECTIVE SURFACE

(75) Inventors: Robert D. Eckles, Malcolm, NE (US); Tyler G. Anderson, Lincoln, NE (US)

(73) Assignee: LI-COR, Inc., Lincoln, NE (US)

(*) Notice: Subject to any disclaimer, the term of this patent is extended or adjusted under 35 U.S.C. 154(b) by 0 days.

(21) Appl. No.: 13/160,405

(22) Filed: Jun. 14, 2011

(65) Prior Publication Data
US 2011/0242659 A1 Oct. 6, 2011

Related U.S. Application Data

(63) Continuation of application No. 11/403,089, filed on Apr. 12, 2006, now Pat. No. 8,018,981.

(51) Int. Cl.
*H01S 3/08* (2006.01)

(52) U.S. Cl. ........... 372/99; 372/92; 372/107; 356/246; 359/507; 359/508; 359/509

(58) Field of Classification Search ............ 372/92, 372/99, 107; 356/246; 359/507, 508, 509
See application file for complete search history.

(56) References Cited

U.S. PATENT DOCUMENTS

| | | | |
|---|---|---|---|
| 4,580,270 A | | 4/1986 | Johnson et al. |
| 4,749,276 A | * | 6/1988 | Bragg et al. ............... 356/246 |
| 4,934,816 A | | 6/1990 | Silver et al. |
| 5,291,265 A | | 3/1994 | Kebabian |
| 5,720,650 A | * | 2/1998 | Mauze et al. ............... 451/75 |
| 5,930,000 A | | 7/1999 | Brand |
| 5,993,560 A | | 11/1999 | Wasak et al. |
| 6,064,488 A | | 5/2000 | Brand et al. |
| 6,188,475 B1 | | 2/2001 | Inman et al. |
| 6,317,212 B1 | | 11/2001 | Eckles |

(Continued)

FOREIGN PATENT DOCUMENTS

| | | | |
|---|---|---|---|
| EP | 1621867 A1 | | 2/2006 |
| JP | 56017736 A | * | 2/1981 |

(Continued)

OTHER PUBLICATIONS

Durry et al., "Open multipass absorption cell for in situ monitoring of stratospheriC trace gas with telecommunication laser diodes," Applied Optics, vol. 41, No. 3, pp. 424-433, Jan. 2002.

(Continued)

*Primary Examiner* — Yuanda Zhang
(74) *Attorney, Agent, or Firm* — Leydig, Voit & Mayer, LLP

(57) ABSTRACT

A multi-pass optical cell with an actuator for actuating a reflective surface is provided. In one preferred embodiment, an apparatus is provided comprising a first reflective surface, a second reflective surface, and a support structure supporting the first and second reflective surfaces. The support structure positions the first and second reflective surfaces to create an optical cell. The apparatus also comprises a source and a detector, which are positioned such that light emitted from the source is reflected in the optical cell at least one time between the first and second reflective surfaces before reaching the detector. The apparatus further comprises an actuator coupled with and operative to actuate the first reflective surface. In some embodiments, the actuator rotates the first reflective surface. Also, in some embodiments, the multi-pass optical cell is an open path multi-pass optical cell, while, in other embodiments, the multi-pass optical cell is a closed path multi-pass optical cell.

31 Claims, 8 Drawing Sheets

U.S. PATENT DOCUMENTS

| | | |
|---|---|---|
| 6,833,542 B2 | 12/2004 | Wang et al. |
| 7,477,377 B2 * | 1/2009 | Silver .......................... 356/246 |
| 2001/0054655 A1 | 12/2001 | Berg et al. |

FOREIGN PATENT DOCUMENTS

| | | |
|---|---|---|
| JP | 58188180 A * | 11/1983 |
| WO | WO 97/49983 | 12/1997 |

OTHER PUBLICATIONS

Herriott et al. "Off-axis paths in spherical mirror interferometers," Applied Optics, vol. 3, No. 4, 523-526, Apr. 1964.

Kebabian et al., "Astigmatic mirror multipass absorption cells for long-path-length spectroscopy," Applied Optics, 34, 3336-3348, 1995.

Kosterev et al., "Chemical Sensors Based on Quantum Cascade Lasers," IEEE Journal of Quantum Electronics, vol. 38, No. 6, pp. 582-591, Jun. 2002.

"Los Gatos Research: Gas Analyzer Theory," httl2:11www.lgrinc.comlIndex.asg?subid=l2th&ProductCategoryID=22,2 pages, printed Apr. 5, 2006.

"Tigeroptics: Principle of Operation," httg:llwww.lgrinc,comlIndex.asg?subid=l2th&ProductCategoryID=22,2 pages, printed Apr. 5, 2006.

"Toptica Photonics: Multipass Cell," 2 pages, May 2002.

White, "Long optical path of large aperture," J. Opt. Soc. Am. 32, 285-288, May 1942.

* cited by examiner

210

CONCAVE-CONCAVE

220

CONCAVE-PLANO

230

CONCAVE-CONVEX

MULTI-PASS OPTICAL CELL WITH ACTUATOR FOR ACTUATING A REFLECTIVE SURFACE

CROSS-REFERENCE TO RELATED APPLICATIONS

This application is a continuation of U.S. patent application Ser. No. 11/403,089, filed Apr. 12, 2006, entitled MULTI-PASS OPTICAL CELL WITH ACTUATOR FOR ACTUATING A REFLECTIVE SURFACE, which is hereby incorporated by reference.

BACKGROUND

Trace gas measurements using laser-based optical absorption techniques frequently use off-axis optical resonators, commonly referred to as Herriott cells. Herriott cells contains reflective surfaces that reflect a light beam multiple times in the cell. In this way, a Herriott cell (and other types of multi-pass optical cells) provides an optical path that is longer than the physical dimension of the cell. This increases absorption and, therefore, decreases detection limits to more easily detect trace gasses in low concentration. A multi-pass optical cell can be a closed path cell (closed to the outside environment) or an open path cell (open to the outside environment). Because open path cells are exposed to the outside environment, the reflective surfaces of open path cells can be subject to contaminants (such as rainwater droplets, dirt, and debris) that can affect the reflection pattern of the light. These cells have an increased sensitivity to such contaminants due to the multiple reflections in the cells. There is a need, therefore, for a multi-pass optical cell with a mechanism for maintaining reflectance of a reflective surface in adverse environmental conditions.

SUMMARY

The present invention is defined by the following claims, and nothing in this section should be taken as a limitation on those claims.

By way of introduction, the preferred embodiments described below provide a multi-pass optical cell with an actuator for actuating a reflective surface. In one preferred embodiment, an apparatus is provided comprising a first reflective surface, a second reflective surface, and a support structure supporting the first and second reflective surfaces. The support structure positions the first and second reflective surfaces to create an optical cell. The apparatus also comprises a source and a detector, which are positioned such that light emitted from the source is reflected in the optical cell at least one time between the first and second reflective surfaces before reaching the detector. The apparatus further comprises an actuator coupled with and operative to actuate the first reflective surface. In some embodiments, the actuator rotates the first reflective surface. Also, in some embodiments, the multi-pass optical cell is an open path multi-pass optical cell, while, in other embodiments, the multi-pass optical cell is a closed path multi-pass optical cell. Other preferred embodiments are provided, and each of the preferred embodiments described herein can be used alone or in combination with one another.

The preferred embodiments will now be described with reference to the attached drawings.

DETAILED DESCRIPTION OF THE PRESENTLY PREFERRED EMBODIMENTS

Figure 1:
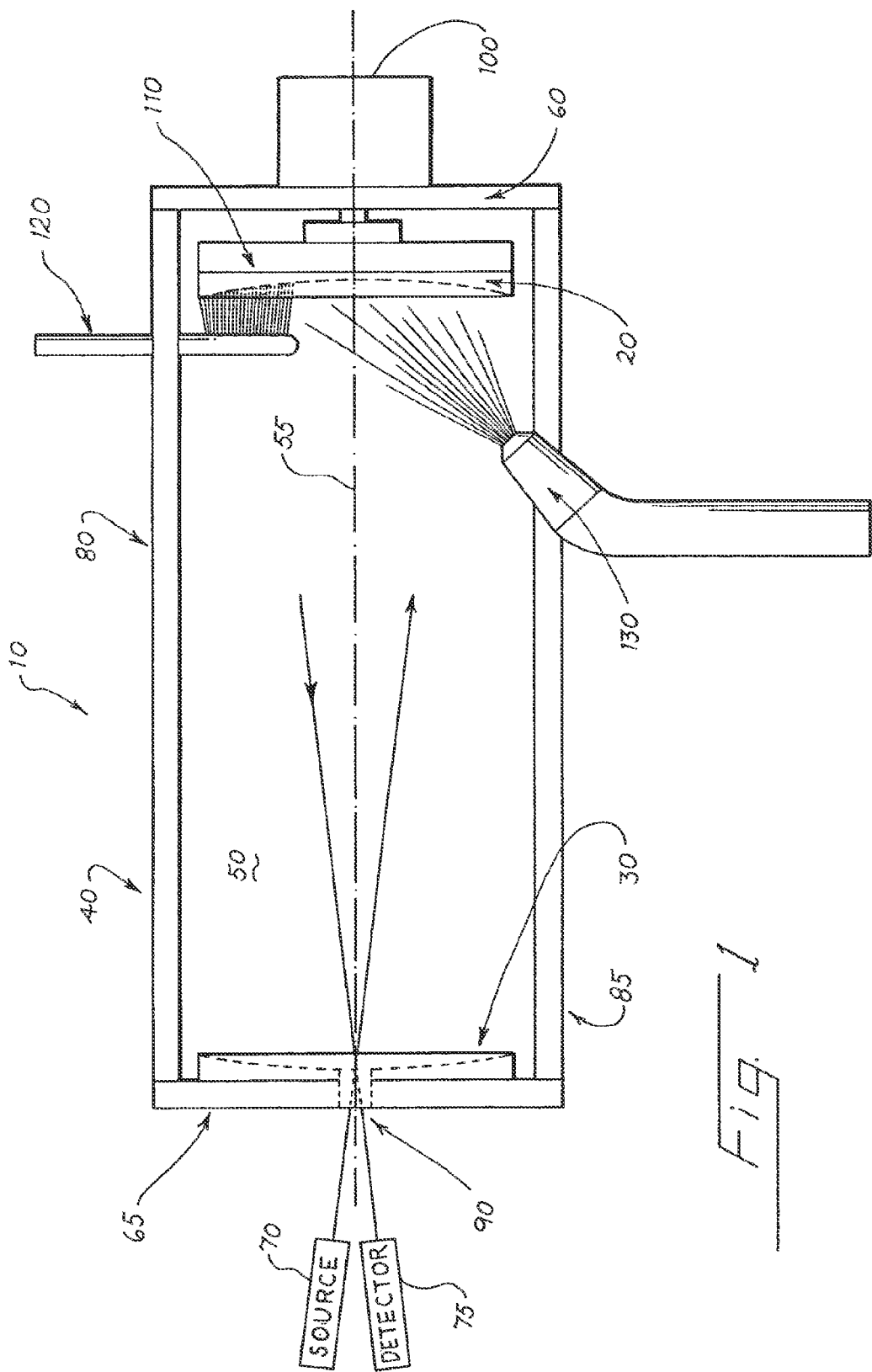
FIG. 1 is an illustration of an apparatus of a preferred embodiment.

Turning now to the drawings, FIG. 1 is an illustration of an apparatus 10 of a preferred embodiment. This apparatus 10 comprises first and second reflective surfaces 20, 30 (i.e., reflective to a wavelength of interest). In this embodiment, the first and second reflective surfaces 20, 30 take the form of mirrors with spherical surface contours. (The mirrors are reflective to a wavelength of interest and may not reflect visible light like a household mirror.) As explained below, other types of reflective surfaces can be used for one or both of the first and second reflective surfaces 20, 30. A support structure 40 supports the first and second reflective surfaces 20, 30 and positions the first and second reflective surfaces 20, 30 away from one another to create an optical cell (or "cavity") 50. It is preferred that the support structure 40 keep the first and second reflective surfaces 20, 30 at a fixed distance apart. An optical axis 55 is defined between the first and second reflective surfaces 20, 30 (here, the optical axis 55 passes through the centers of radii of the first and second reflective surfaces 20, 30). Accordingly, the optical cell 50 is axially symmetric in that the first and second reflective surfaces 20, 30 are symmetric about the optical axis 55. In this embodiment, the support structure 40 comprises first and second support bases 60, 65, which support the first and second reflective surfaces 20, 30, respectively, and a plurality of structural support rods 80, 85. While the support structure 40 in this embodiment comprises two structural support rods 80, 85, as described below, in other embodiments, more than two (e.g., three or four) structural support rods or just a single support rod can be used.

The second support base 65 also supports a light source 70 (e.g., a laser) and a detector 75. (FIG. 1 shows the light source 70 and detector 75 positioned away from the second support base 65 for illustrative purposes to more clearly show the light beams. However, in other embodiments, the light source and detector can actually be positioned away from the second support base.) A passage 90 is located in the second support base 65 to allow light from the source 70 and to the detector 75 to pass through the second support base 65. As an alternative to using a passage 90 in the second support base 65, additional reflective surfaces can be used to introduce light into the cell and/or cause light to exit the cell. With this alternative, the source and/or detector can be located in a different location.)

The source 70 and detector 75 are positioned such that light emitted from the source 70 is reflected in the optical cell 50 at least one time between the first and second reflective surfaces 20, 30 before passing back through the passage 90 and reaching the detector 75. In other words, the optical cell 50 is a multi-pass optical cell. It should be noted that a multi-pass cell is an optical resonator because it is a device that allows light to reflect many times in the cell (or cavity) between opposing reflective surfaces. If the cavity in the optical resonator comprises a gain medium, then a laser can be realized. If the cavity in the optical resonator comprises an absorbing medium, then an absorption measurement cell can be realized. If the cavity is empty, then a Fabry-Perot interferometer can be realized.

Figure 2A:
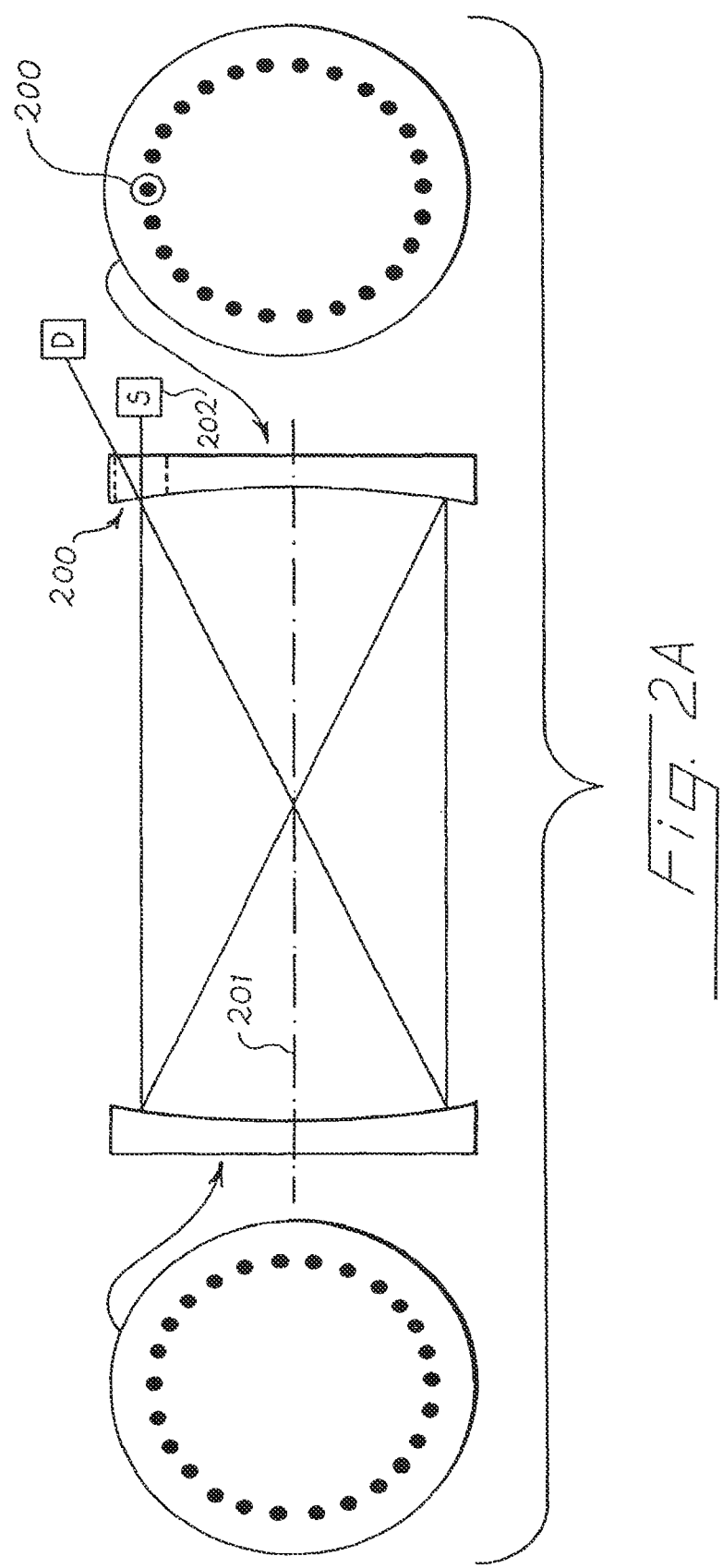
FIGS. 2A-2D are illustrations of optical cell alignments and mirror types of a preferred embodiment.
Figure 2B:
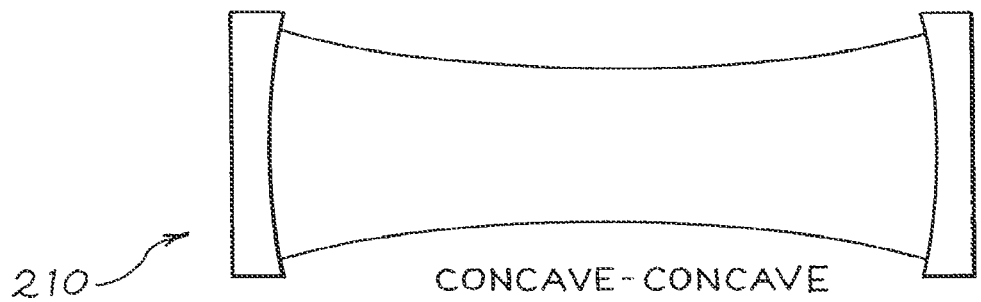
Figure 2C:
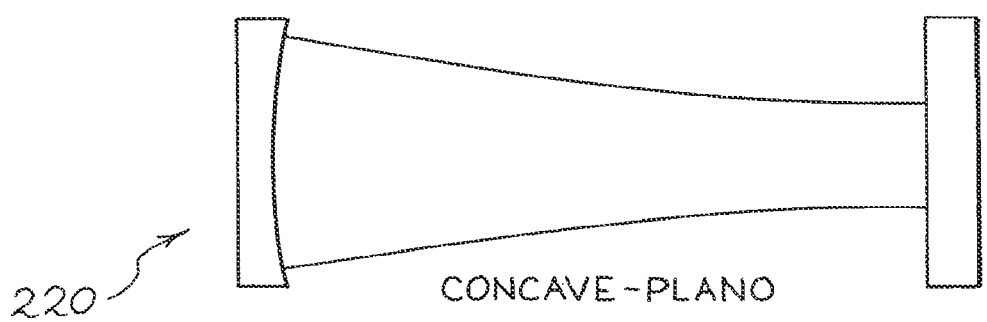
Figure 2D:
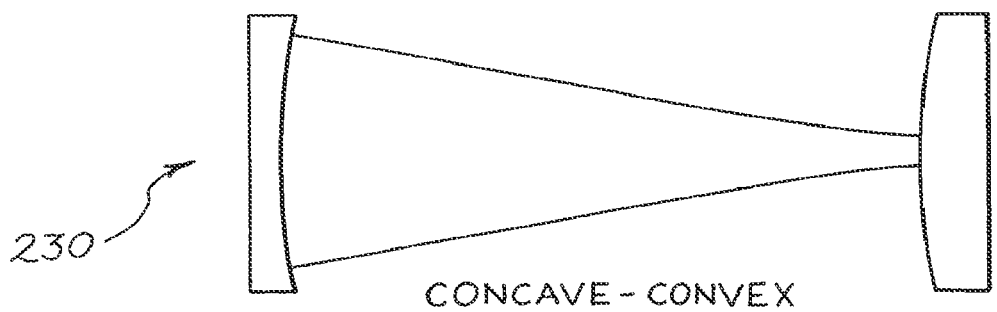

To obtain multiple reflections in the optical cell 50, the source 70 introduces light into the optical cell 50 in direction other than along the optical axis 55 (i.e., in an "off-axis" location). The source 70 can introduce light along the optical axis 55 if the light is reflected by an entrance window or some other component before entering the optical cell 50. As shown in FIG. 2A, because of the spherical surface contour of the first and second reflective surfaces, when light is introduced into a multi-pass cell in an off-axis location, a circular reflection (or "bounce") pattern is created on the first and second reflective surfaces 20, 30. This circular bounce pattern can be achieved with several types of mirror shapes, such as concave-concave 210 (FIG. 2B), concave-plano 220 (FIG. 2C), and concave-convex 230 (FIG. 2D), with the different mirror shapes providing a different number of reflections in, and a different diameter size of, the bounce pattern.

Figure 2E:
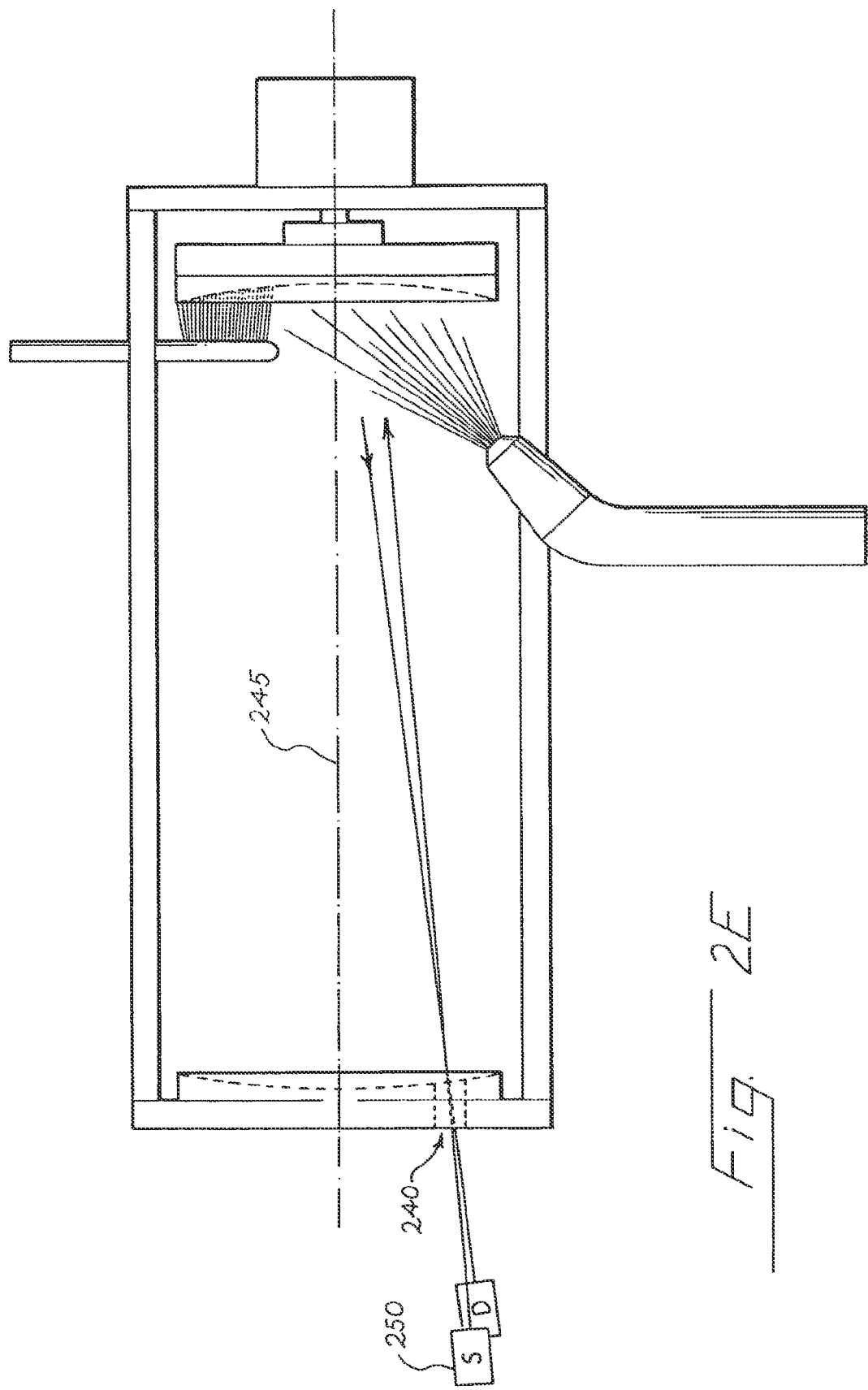
FIG. 2E is an illustration of an apparatus of another preferred embodiment.

It should be noted that FIG. 2A shows a different location of the passage 200 than in FIG. 1. Since this passage 200 is not along the optical axis 201, the source 202 can be positioned to introduce light along the axis of the passage 200 (which is parallel to the optical axis 201), in contrast to the design shown in FIG. 1, where the axis of the passage 90 is the optical axis 55. In another alternative (shown in FIG. 2E), the passage 240 is not along the optical axis 245, and the source 250 is positioned to introduce light off axis to both the optical axis 245 and the axis of the passage 240.

Returning now to FIG. 1, in this embodiment, the source 70 and detector 75 are used to measure a concentration of a gas (e.g., methane) in the optical cell 50. The concentration of the gas in the optical cell 50 can be determined by examining the degree to which certain wavelengths of light are absorbed by the sample in the optical cell 50. The optical cell 50 can be closed to the outside environment (a "closed path" application); however, in this embodiment, the support structure 40 is an open frame designed to allow the optical cell 50 to be open to the outside environment (an "open path" application). Because the optical cell 50 is used in an open-air environment, the reflective surfaces 20, are subject to contaminants (such as rainwater droplets, dirt, and debris) that can affect the reflection pattern of the light and the overall accuracy of the apparatus 10. For example, if the reflection pattern is sufficiently disturbed, the light may be reflected away from the passage 90 and not reach the detector 75.

To address this issue, the apparatus 10 in FIG. 1 contains an actuator 100 supported by the first support base 60 and coupled to the first reflective surface 20 through a spindle 110, which is used to mount and level the first reflective surface 20. (As used herein, the phrase "coupled with" means directly coupled with or indirectly coupled with through one or more named or unnamed components.) The actuator 100 is operative to actuate the first reflective surface 20 to at least partially remove contaminants from the first reflective surface 20, reducing their effect on the apparatus's operation. As used herein, the term "actuator" broadly refers to any device used to directly or indirectly move another device (and, thus, is operative to actuate (or, in some situations, rotate) the first reflective surface 20). An actuator can take any suitable form, including, but not limited to, a motor, a linear actuator, a piston, a rack-and-pinion device, and systems that use hydraulic fluids. An actuator "actuates" the first reflective surface 20 by moving the first reflective surface 20 in any suitable manner, including, but not limited to, rotating the first reflective surface 20, vibrating the first reflective surface 20, or linearly moving the first reflective surface 20 rapidly back and forth. The actuator 100 can also linearly move the first reflective surface 20 to adjust the distance to the second reflective surface 30. While not required in all embodiments, the actuator 100 can also be operative to track the position of the first reflective surface 20 so that, after actuation, the actuator 100 will return the first reflective surface 20 to substantially the same position as before actuation.

It should be noted that, in some embodiments, the actuator actuates the first reflective surface (i.e., actuates in any suitable form of actuation). In other embodiments, the actuator rotates the first reflective surface. Accordingly, the term "actuate" in the claims should not be limited to rotate. Also, actuators other than a motor (such as those listed above) can be used to rotate the first reflective surface. Accordingly, the phrase "actuator operative to rotate" in the claims should not be limited to a motor.

In the embodiment shown in FIG. 1, the actuator 100 takes the form of a motor that rotates the first reflective surface 20 to "spin off" rainwater droplets, dirt, debris and/or other contaminants from the first reflective surface 20. Also in this embodiment, the axis of rotation of the motor shaft lies on the optical axis 55. Because the first reflective surface 20 has a spherical surface contour (creating a circular bounce pattern) and rotates about the optical axis 55, the stopping position of the first reflective surface 20 can be at a different angular location than the starting position without distorting the bounce pattern. In other words, because of its spherical surface, the first reflective surface 20 can be rotated or spun about its center of curvature (along the optical axis 55) and still maintain the bounce pattern even if the first reflective surface 20 is at a different angular position after actuation. Moving the first reflective surface 20 rapidly back and forth in a linear direction along the optical axis 55 would also not distort the bounce pattern since the travel is along the optical axis 55 (provided that, after actuation, the first reflective surface 20 is returned to a position substantially the same distance from the second reflective surface 30), neither would other types of actuation (e.g., vibration, "off axis" rotation, etc.) provided that the actuator 100, after actuation, positions the center of radius of the first reflective surface 20 back into alignment with the optical axis 55 and return the first reflective surface 20 to a position substantially the same distance from the second reflective surface 30 as before actuation.

While any suitable components can be used, it is presently preferred that the first and second reflective surfaces 20 be spherical mirrors with 4 inch diameters and 15 inch focal lengths. The second reflective surface contains a 0.3 inch diameter hole 1.5 inches away from the center of the mirror. The preferred coating on the first and second reflective surfaces is a thin film dielectric stack coating optimized for 1.651 micro meter. It is preferred that the support structure 40 comprise a single structural support rod along the perimeter of the optical cell 50 and that the support structure 40 position the first and second reflective surfaces 20, 30 about 20 inches apart, to create an optical cell 50 length of 20 inches. It is also presently preferred that the light source 70 be a Vertical Cavity Surface Emitting Laser (VCSEL) laser diode. The laser wavelength is 1.651 micro meter, which corresponds to a suitable methane absorption line. The laser power output is typically greater than 100 micro Watt. The detector 75 is preferably an InGaAs PIN photodiode, Hamamatsu part number G8421-03, which has suitable sensitivity to the laser emission. Also, it is preferred that the optical path length be 30 meters to provide 60 bounces. Further, it is preferred that the actuator 100 be a brushless DC motor with approximately 20 Watt output power with preloaded ball bearings and 0 to 2000 RPM capability. As mentioned above, these are merely presently preferred components, and the following claims should not be limited to the specific examples provided.

To further maintain the cleanliness of the first reflective surface 20 and maintain the operation of the apparatus 10 in an otherwise adverse or disabling environment, the apparatus 10 can contain an optional cleaning mechanism. (The cleaning mechanism is optional and should not be read into the claims unless explicitly recited therein.) For example, as shown in FIG. 1, the cleaning mechanism can comprise a retractable brush 120 and/or a cleaning fluid (e.g., ethynol and water) spray nozzle 130. The actuation (e.g., spinning) of the first reflective surface 20 helps dry and remove the cleaning fluid from the first reflective surface 20. The cleaning mechanism can comprise additional or alternative components such as a cloth, a sponge, and an air nozzle.

In addition to or as an alternative to actuating the first reflective surface 20, the apparatus 10 can contain an actuator to actuate the second reflective surface 30 (e.g., in designs where the second reflective surface 30 is not well-isolated from the elements). However, if the axis of the passage 90 is not along the optical axis 55, it is preferred that that actuator keep track of the position of the second reflective surface 30 and use an index, stop, or other mechanism to ensure that the stopping position of the second reflective surface 30 is at substantially the same angular location as in the starting position. Otherwise, the passage 90 may not align with the source 70 and detector 75. Since the first reflective surface 20 does not contain a passage, similar care is not needed when rotating the first reflective surface 20 in this embodiment.

As described above, actuating one or both of the first and second reflective surfaces helps maintain reflectance of those surfaces in adverse environmental conditions. For example, an experiment was conducted in which an optical cell was set up for 60 passes. A rain/dust event deposited dirt onto the first reflective surface that reduced the throughput to about 1%. The first reflective surface was spun up to 2,000 RPM, and a mix of alcohol and water was squirted onto it for a few seconds. Most of the dirt was removed, although some material still remained. However, the throughput after cleaning was about 50%, which is a very usable amount. It should be noted that, as an alternative to actuating the reflective surface(s) to remove contaminants after contamination, the actuator can continuously actuate the reflective surface(s) to help avoid contamination of the reflective surface(s) in the first place. In this way, the actuator can serve as a preventive measure instead of a cure.

Figure 3:
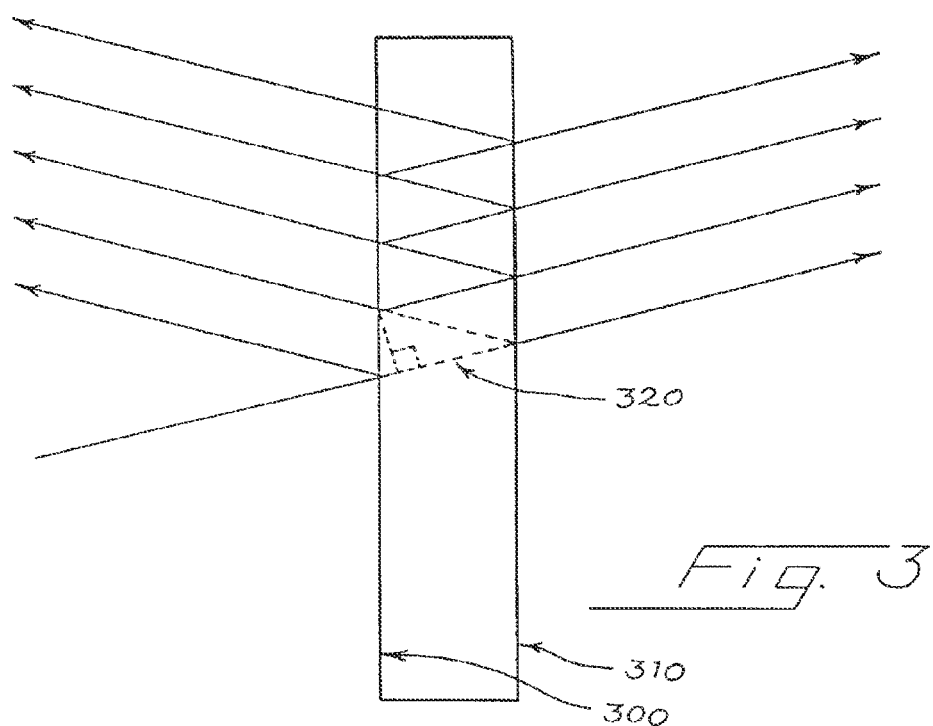
FIG. 3 is an illustration showing a single light ray and how multiple beam interference can be caused by parallel reflecting surfaces.

Actuating one or both of the first and second reflective surfaces can also help reduce etalons. An etalon is two reflective surfaces 300, 310 parallel to each other (see FIG. 3), FIG. 3 is a diagram of a single light ray passing through a window. For simplicity, the diagram is drawn without any refraction effects from the window. As a ray of light passes through, a large percentage is transmitted. However, what is not transmitted is reflected. This is shown by the extra path 320. Those reflections can propagate through the window and exit with the same trajectory as the original beam. The extra beams have traveled a different distance than the original beam and are, therefore, out of phase. Since the light is coherent, it will constructively or destructively interfere.

In wavelength modulation spectroscopy, as the wavelength changes, so does the amount of interference. The amplitude of the signal will therefore modulate with the wavelength. This causes a false signal that can have frequency components similar to the actual signal from a gas under investigation (e.g., methane). Etalons are most common in transmissive optics but can occur from any reflective surface and through any refracting medium. If an etalon occurs between two optical elements, generally, the etalon is unstable. Simply touching or applying pressure to the side of the component may be enough to move the etalon's signal. With reference to the apparatus 10 in FIG. 1, the first and second reflective surfaces 20, 30 preferably have slight optical variations from construction and alignment. Accordingly, when one or both of those surfaces 20, 30 are actuated (e.g., rotated), the optical variations would serve to randomize etalon fringes when monochromatic light is passed through the cell 50.

Figure 4:
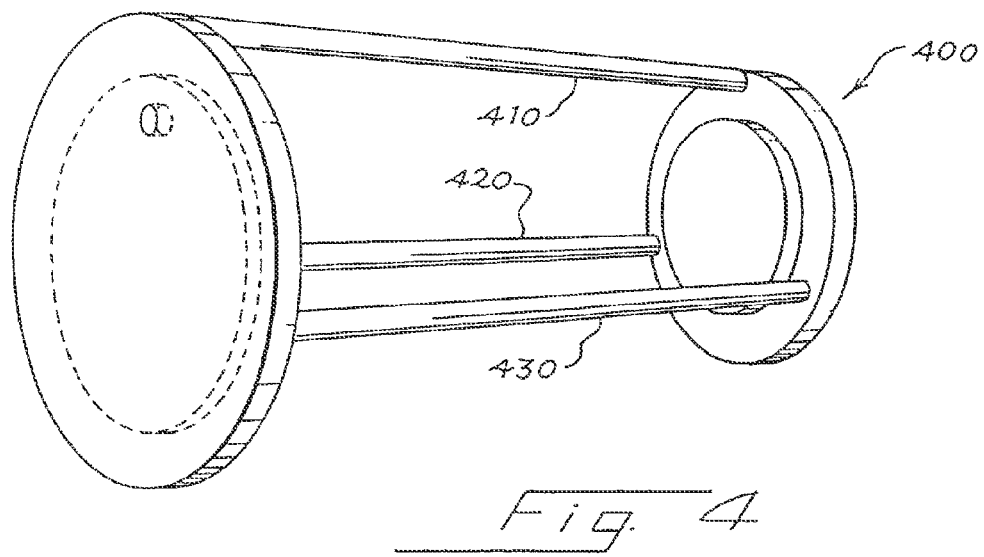
FIG. 4 is an illustration of an apparatus of a preferred embodiment using three structural support rods.
Figure 5:
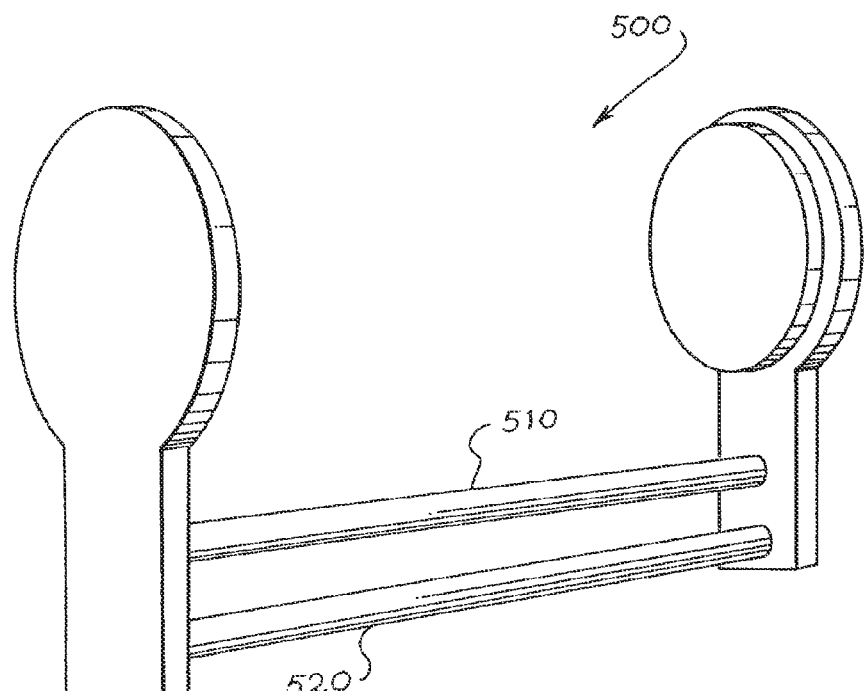
FIG. 5 is an illustration of an apparatus of a preferred embodiment using a single structural support rod along a perimeter of an optical cell.

There are several alternatives that can be used with this embodiment. For example, in the embodiment shown in FIG. 1, the support structure 40 contained two structural support rods 80, 85. In alternate embodiments, more than two structural support rods can be used. For example, FIG. 4 is an illustration of an apparatus 400 with three structural support rods 410, 420, 430. However, it is presently preferred that the support structure contain only a single support rod along the perimeter of the optical cell to minimize the disturbance of the wind profile. For example, the support structure in the apparatus 500 shown in FIG. 5 is a "C-clamp" design, where a single support rod 510 is along the perimeter of the optical cell. Using a single structural support rod along the perimeter of the optical cell helps minimize flow distortion and air turbulence in the optical cell caused by the structure support rod. (A second support rod 520 is used for additional support, but it is located "behind" support rod 510—not along the perimeter of the optical cell. Accordingly, there is only air flow distortion in one direction.)

Figure 6:
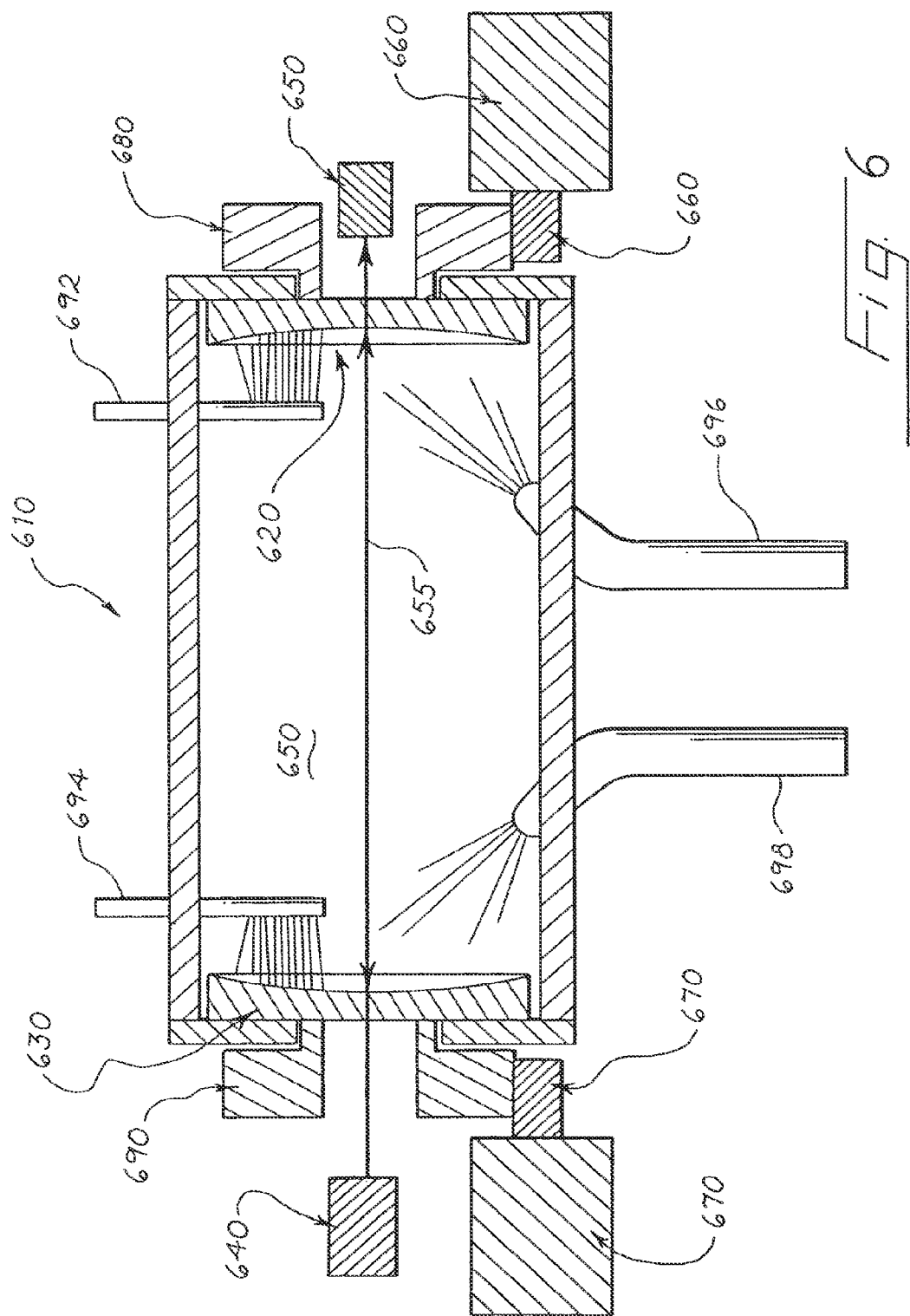
FIG. 6 is an illustration of a ring-down cavity of a preferred embodiment.

Other alternatives are possible. For example, the multi-pass optical cell 10 in FIG. 1 took the form of a Herriott cell. A Herriott cell contains two spherical reflective surfaces with light being provided in an off-axis location, which provide a circular bounce pattern. A Herriott cell has an axially symmetric optical cavity because it is symmetric about the center line axis between the two mirrors (i.e., the optical axis). However, other types of multi-pass optical cells can be used, such as, but not limited to, a ring-down cavity, an astigmatic Herriott cell, and a White cell. Each of these alternatives will now be described FIG. 6 is an illustration of a ring-down cavity 610 of a preferred embodiment. As shown in FIG. 6, like the Herriott cell 10 shown in FIG. 1, the ring-down cavity the optical cell 650 is axially symmetric about the optical axis 655. However, in the ring-down cavity 610, the source 640 is positioned such that light enters the optical cell 650 along the optical axis 655 (although, in other embodiments, light can enter off axis). The first reflective surface 620 allows some light to pass through to the detector 650, while reflecting light back to the second reflective surface 630. Light bounces back and forth between the first and second reflective surfaces 620, 630, with light transmitted through the first reflected surface 620 being detected by the detector 650 with each bounce.

Because of the design of the ring-down cavity 610, it is preferred that both the first and second reflective surfaces 620, 630 be actuated. Accordingly, in this embodiment, the first and second actuators 660, 670 are coupled with the first and second reflective surfaces 620, 630, respectively. Specifically, in this embodiment, the first and second actuators 660, 670 take the form of motors that are coupled to the first and second reflective surfaces 620, 630 through gears attached to the motors 660, 670 and hollow gears 680, 690 attached to the first and second reflective surfaces 620, 630, respectively. Because of the design of a ring-down cavity, it is preferred that, after actuation, the first and second reflective surfaces 620, 630 be returned to the same relative positions with respect to each other as before actuation. Accordingly, in this embodiment, it is preferred that the actuators 660, 670 keep track of the position of the first and second reflective surfaces 620, 630 and use an index, stop, or other mechanism to control the stopping positions after actuation of the first and second reflective surfaces 620, 630. Also, as with the apparatus in FIG. 1, the ring-down cavity 610 in this embodiment contains the optional cleaning mechanism of retractable brushes 692, 694 and cleaning fluid spray nozzles 696, 698.

Figure 7:
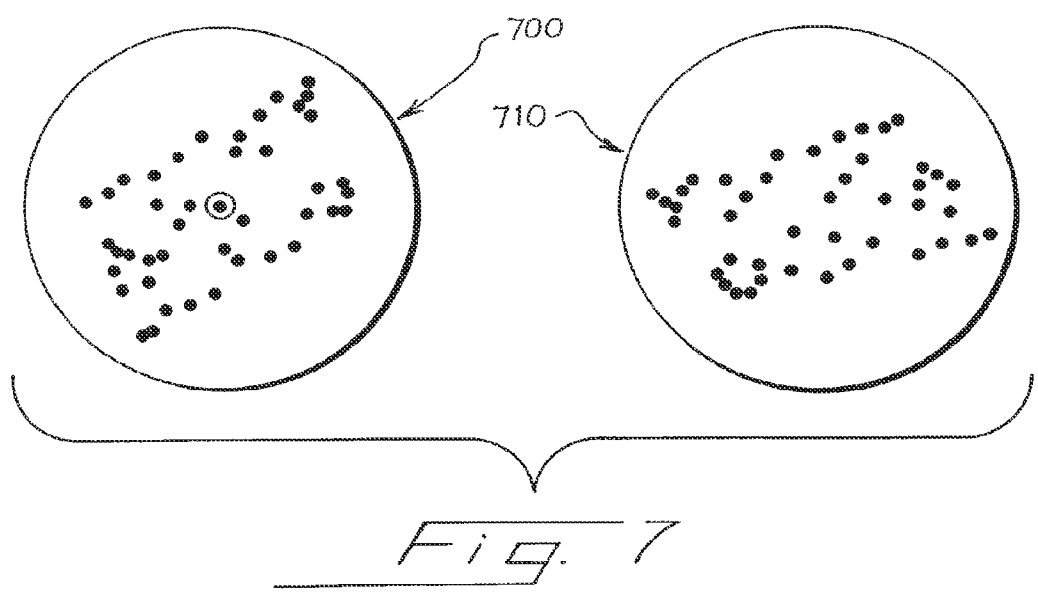
FIG. 7 is an illustration of a bounce pattern using two cylindrical or two astigmatic reflective surfaces.

An astigmatic Herriott cell looks like the Herriott cell 10 shown in FIG. 1 but uses reflective surfaces that have astigmatism in them to give a non-circular bounce pattern. Specifically, an astigmatic Herriott cell produces a non-symmetrical Lissajous bounce pattern (to provide a longer optical path) that requires precise alignment between both reflective surfaces. This is shown in the bounce patterns 700, 710 in FIG. 7. (The same bounce patterns occur with two cylindrical lens.) Accordingly, for such cells, it is preferred that the actuator keep track of the starting position of the reflective surfaces and return the reflective surfaces to substantially the same position after actuation.

Figure 8:
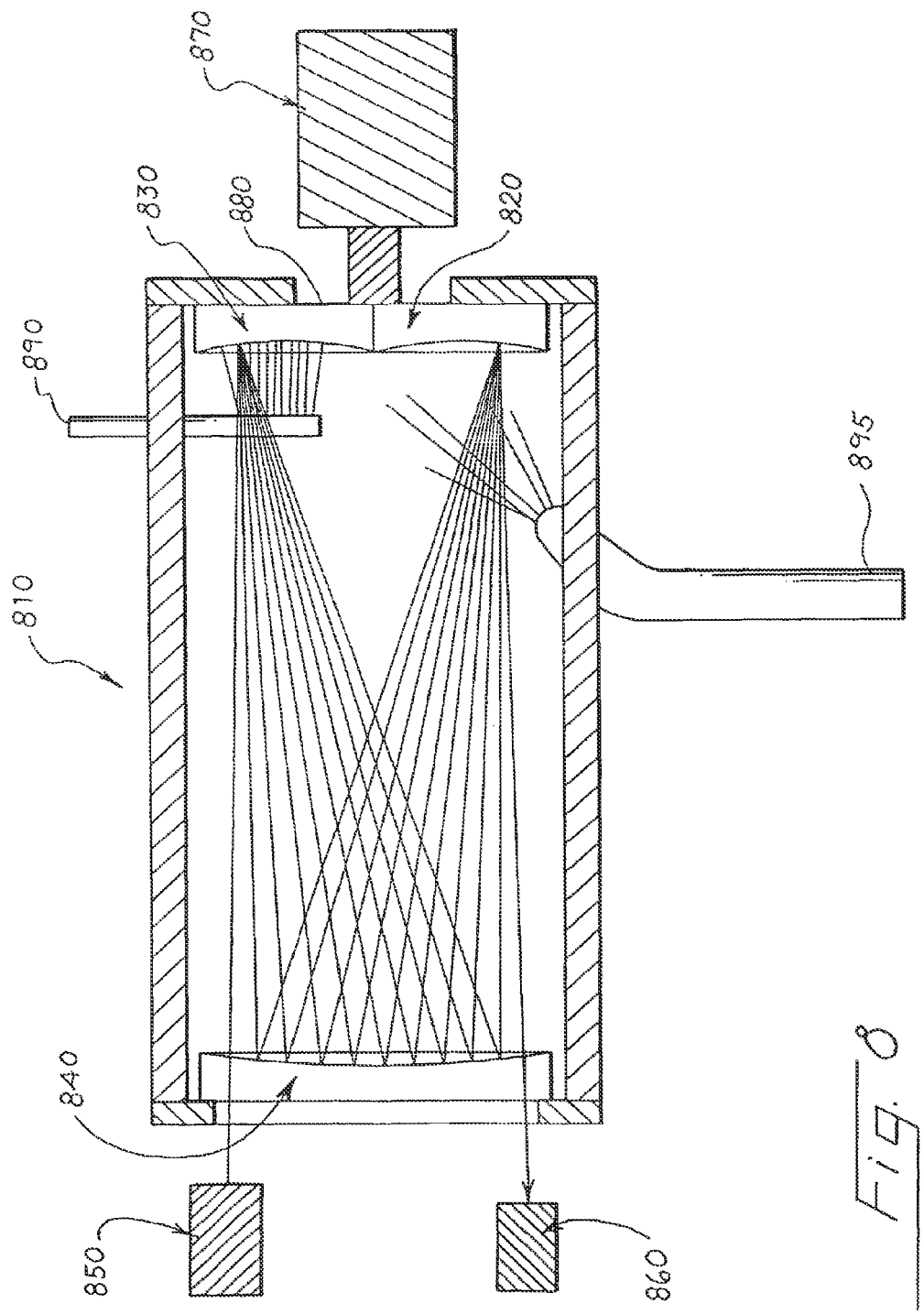
FIG. 8 is an illustration of a White cell of a preferred embodiment.

Turning again to the drawings, FIG. 8 is an illustration of a White cell 810 of a preferred embodiment. As shown in FIG. 8, in contrast to the multi-pass optical cells discussed so far, the White cell 810 comprises three reflective surfaces: first, second, and third reflective surfaces 820, 830, 840 (e.g., mirrors with spherical surfaces). The source 850 and detector 860 are positioned to provide the bounce pattern shown in the drawing. In this embodiment, an actuator 870 (e.g., a motor) is coupled to the first and second reflective surfaces 820, 830 through a spindle 880, which is used to mount and level the first and second reflective surfaces 820, 830. Because of the design of a White cell, it is preferred that the first and second reflective surfaces 820, 830 be returned to the same relative positions with respect to the third reflective surface 840 after actuation. Accordingly, in this embodiment, it is preferred that the actuator 870 keep track of the position of the first and second reflective surfaces 820, 830 and use an index, stop, or other mechanism to control the stopping position after actuation of the first and second reflective surfaces 820, 830. Also, as with the apparatus in FIG. 1, the White cell 810 in this embodiment contains the optional cleaning mechanism of a retractable brush 890 and cleaning fluid spray nozzle 895.

It should be noted that the above embodiments can be used in any suitable application. For example, the apparatus can be used as an open path sensor for measuring naturally occurring methane concentrations at a frequency and resolution suitable for calculating flux by turbulent transport in the open atmosphere. The apparatus can achieve sensitivity by using an appropriate tunable diode laser that operates at a temperature accessible by TE coolers and roughly a 50 m path length. Depending upon the sensitivity required, the laser can be a 1.6 um InGaAs communication laser or a more expensive 2.3 um antimonide DFB laser. Both types are readily available. The long path length is achieved with an optical system consisting of appropriately designed mirrors that steer the light pattern giving the number of bounces required to obtain the specified path length. The laser is tuned to a frequency near the line of interest by adjusting the temperature, and output wavelength range is varied at high frequency, and the data is analyzed by a technique that is similar to taking first and second derivatives of the peak. Both AC and DC components of the laser output and gas absorption are measured allowing corrections to be made for variations in laser output. This provides long-term stability in the measurements.

Other gases (such as water vapor) can be measured simultaneously with a methane measurement. This would allow dilutions corrections to be made, and it would support eddy covariance measurements of ecosystem energy balance, which may be relevant when methane flux is measured. Other combinations of gases can also be measured, such as CH4+H2O+CO2, CH4+NH3, CH4+CO, $N_2O$ (nitrous oxide), $C^{13}O_2$ (carbon isotope 13 dioxide), and $H_2O^{18}$ (water vapor, oxygen isotope 18). Methane and water vapor can be measured together with a single laser, but some of the other combinations may require two lasers. Thus, it may be desired to design the apparatus to support two lasers.

While the design of the apparatus is open path, there are times when a closed path approach is desirable. To convert the open path apparatus to a closed path apparatus, a shroud can be placed around the open path apparatus. This would protect the reflective surfaces from environmental contamination and would allow operation at reduced pressure, which can improve resolution. It is desirable to keep the light reflection pattern on the reflective surfaces as compact as possible in order to minimize optical cell volume and gas flow response time when the apparatus is used in the closed configuration.

It is preferred that the apparatus have low power consumption (e.g., such that it can run on solar cells and battery power), high resolution to measure low methane fluxes, and a high frequency response suitable for eddy covariance measurements. Specifically, it is presently preferred that the apparatus have a power of 10 Watts, a frequency response of 10 Hz, and an rms signal resolution of 10 ppb. It should again be noted that the foregoing was a description of one of many suitable applications and should not be read as a limitation on the claims.

It is important to note that any of the various aspects of the preferred embodiments can be used alone or in combination. Finally, the use of "first," "second," etc. in the above description was for illustrative purposes only, and components in the claims that are labeled "first," "second," etc. should not interpreted as necessarily referring to the same "first," "second," etc. component described in this specification.

It is intended that the foregoing detailed description be understood as an illustration of selected forms that the invention can take and not as a definition of the invention. It is only the following claims, including all equivalents, that are intended to define the scope of this invention.

What is claimed is:

1. An apparatus comprising:
a first reflective surface;
a second reflective surface;
an open frame support structure supporting the first and second reflective surfaces and positioning the first and second reflective surfaces to create an open path optical cell;
a source;
a detector, wherein the source and detector are positioned such that light emitted from the source is reflected in the optical cell at least one time between the first and second reflective surfaces before reaching the detector, wherein the light emitted from the source enters the optical cell through the second reflective surface; and an actuator coupled with and operative to periodically actuate the first reflective surface to remove contaminants from the first reflective surface.

2. The apparatus of claim 1, wherein the actuator comprises a motor operative to rotate the first reflective surface.

3. The apparatus of claim 1, wherein the actuator is operative to, after actuation, return the first reflective surface to substantially the same position as before actuation.

4. The apparatus of claim 1 further comprising a second actuator coupled with and operative to actuate the second reflective surface.

5. The apparatus of claim 4, wherein the second actuator comprises a motor operative to rotate the second reflective surface.

6. The apparatus of claim 4, wherein the second actuator is operative to, after actuation, return the second reflective surface to substantially the same position as before actuation.

7. The apparatus of claim 1 further comprising a cleaning mechanism.

8. The apparatus of claim 7, wherein the cleaning mechanism comprises a retractable brush.

9. The apparatus of claim 7, wherein the cleaning mechanism comprises a cleaning fluid spray nozzle.

10. The apparatus of claim 1, wherein an optical axis passes through centers of radii of the first and second reflective surfaces, and wherein the source emits light into the optical cell along the optical axis.

11. The apparatus of claim 1, wherein the support structure comprises a plurality of structural support rods.

12. The apparatus of claim 1, wherein the support structure comprises a single structural support rod along a perimeter of optical cell.

13. The apparatus of claim 1, wherein the optical cell comprises a Herriott cell.

14. The apparatus of claim 1, wherein the optical cell comprises a ring-down cavity.

15. The apparatus of claim 1, wherein the optical cell comprises an astigmatic Herriott cell.

16. The apparatus of claim 1, wherein the optical cell comprises a White cell.

17. An apparatus comprising:
a first reflective surface;
a second reflective surface;
an open frame support structure supporting the first and second reflective surfaces and positioning the first and second reflective surfaces to create an open path optical cell;
a source;
a detector, wherein the source and detector are positioned such that light emitted from the source is reflected in the optical cell at least one time between the first and second reflective surfaces before reaching the detector, wherein the light emitted from the source enters the optical cell through the second reflective surface; and
means for periodically actuating the first reflective surface to remove contaminants from the first reflective surface.

18. The apparatus of claim 17, wherein the means for actuating the first reflective surface comprises a motor.

19. An apparatus comprising:
a first reflective surface;
a second reflective surface;
a support structure supporting the first and second reflective surfaces and positioning the first and second reflective surfaces to create an optical cell;
a source;
a detector, wherein the source and detector are positioned such that light emitted from the source is reflected in the optical cell at least one time between the first and second reflective surfaces before reaching the detector, wherein the light emitted from the source enters the optical cell through the second reflective surface; and
means for periodically rotating the first reflective surface to remove contaminants from the first reflective surface.

20. The apparatus of claim 19, wherein the means for rotating the first reflective surface comprises an actuator.

21. The apparatus of claim 19, wherein the means for rotating the first reflective surface comprises a motor.

22. A multi-pass optical cell comprising:
a first mirror;
a second mirror, wherein an optical axis passes through centers of radii of the first and second mirrors;
an open frame support structure supporting the first and second mirrors and positioning the first and second mirrors to create an open path optical cell;
a source positioned to emit light into the optical cell in a direction other than along the optical axis;
a detector, wherein light emitted from the source is reflected in the optical cell at least one time between the first and second mirrors before reaching the detector, wherein the light emitted from the source enters the optical cell through the second mirror; and
a motor coupled with the first mirror, wherein the motor comprises a motor shaft lying on the optical axis and is operative to periodically rotate the first mirror about the optical axis to remove contaminants from the first reflective surface.

23. The multi-pass optical cell of claim 22 further comprising a second motor coupled with the second mirror, wherein the second motor comprises a second motor shaft lying on the optical axis and is operative to rotate the second mirror about the optical axis.

24. The multi-pass optical cell of claim 22 further comprising a cleaning mechanism.

25. The multi-pass optical cell of claim 24, wherein the cleaning mechanism comprises a retractable brush.

26. The multi-pass optical cell of claim 24, wherein the cleaning mechanism comprises a cleaning fluid spray nozzle.

27. The multi-pass optical cell of claim 22, wherein the first mirror comprises a spherical surface and a circular bounce pattern is created on the first and second mirrors.

28. An apparatus comprising:
a first reflective surface;
a second reflective surface;
an open frame support structure supporting the first and second reflective surfaces and positioning the first and second reflective surfaces to create an open path optical cell;
a source;
a detector, wherein the source and detector are positioned such that light emitted from the source is reflected in the optical cell at least one time between the first and second reflective surfaces before reaching the detector, wherein the light emitted from the source enters the optical cell through the second reflective surface; and
a cleaning mechanism for periodically cleaning the first reflective surface, wherein the cleaning mechanism includes a fluid spray nozzle, and wherein the cleaning mechanism further includes an actuator coupled with and operative to periodically actuate the first reflective surface.

29. The apparatus of claim 28, wherein the fluid spray nozzle includes an air spray nozzle.

30. The apparatus of claim 1, wherein the actuator is operative to vibrate the first reflective surface.

31. The apparatus of claim 1, wherein the actuator is operative to rapidly move the first reflective surface back and forth along an optical axis defined by the first and second reflective surfaces.

* * * * *